United States Patent
Hehrlein (10) Patent No.: US 10,898,355 B2
(45) Date of Patent: Jan. 26, 2021

(54) BIORESORBABLE STENT

(71) Applicant: ALBERT-LUDWIGS-UNIVERSITÄT FREIBURG, Freiburg (DE)

(72) Inventor: Christoph Hehrlein, Freiburg i. Br (DE)

(73) Assignee: ALBERT-LUDWIGS-UNIVERSITÄTFREIBURG, Freiburg (DE)

(*) Notice: Subject to any disclaimer, the term of this patent is extended or adjusted under 35 U.S.C. 154(b) by 0 days.

(21) Appl. No.: 14/777,239

(22) PCT Filed: Mar. 13, 2014

(86) PCT No.: PCT/EP2014/000672
§ 371 (c)(1),
(2) Date: Sep. 15, 2015

(87) PCT Pub. No.: WO2014/146769
PCT Pub. Date: Sep. 25, 2014

(65) Prior Publication Data
US 2016/0022450 A1   Jan. 28, 2016

(30) Foreign Application Priority Data

Mar. 16, 2013  (DE) .................. 10 2013 004 625

(51) Int. Cl.
*A61F 2/90*  (2013.01)
*A61F 2/856*  (2013.01)
(Continued)

(52) U.S. Cl.
CPC ............. *A61F 2/90* (2013.01); *A61F 2/844* (2013.01); *A61F 2/856* (2013.01); *A61L 31/148* (2013.01);
(Continued)

(58) Field of Classification Search
CPC ............. A61F 2/90; A61F 2210/0004; A61F 2250/003; A61F 2250/0036;
(Continued)

(56) References Cited

U.S. PATENT DOCUMENTS 7,588,597 B2 *  9/2009  Frid .......................... A61F 2/90
                                                        623/1.51
8,109,991 B2    2/2012  Clifford et al.
(Continued)

FOREIGN PATENT DOCUMENTS

DE   102005018356 A1   10/2006
DE   102010027124 A1    1/2012
(Continued)

OTHER PUBLICATIONS

International Search Report for International Application No. PCT/EP2014/000672 dated Jun. 5, 2015.

*Primary Examiner* — Brian E Pellegrino
(74) *Attorney, Agent, or Firm* — Fitch, Even, Tabin & Flannery LLP (57) ABSTRACT

A stent having a tubular framework structure consisting of interconnected stent struts, fabricated as a whole from a bioresorbable material and being convertible from a compressed first geometric shape into a radially dilated, dimensionally stable, tubular second geometric shape.

Characterized by all of the stent struts of the tubular framework structure has made of a uniform bioresorbable material, the tubular framework structure comprises at least one surface region, which is congruent in one piece and is situated on a lateral cylindrical surface the surface, region comprising stent struts surrounded by stent struts of the framework structure that are adjacent to the surface region, such that the stent struts within the surface region have a smaller amount by weight of bioresorbable material per one (Continued)

predefinable discrete strut length, than the stent struts of the framework structure adjacent to the surface regions.

34 Claims, 2 Drawing Sheets

(51) Int. Cl.
　　*A61L 31/14* (2006.01)
　　*A61F 2/844* (2013.01)
(52) U.S. Cl.
　　CPC .............. *A61F 2210/0004* (2013.01); *A61F 2230/0069* (2013.01); *A61F 2250/003* (2013.01); *A61F 2250/0032* (2013.01); *A61F 2250/0035* (2013.01)
(58) Field of Classification Search
　　CPC ...... A61F 2002/821; A61F 2310/00389; A61F 2/856; A61F 2/82; A61L 31/148; A61L 31/12; A61L 27/58
　　See application file for complete search history.

(56) References Cited

U.S. PATENT DOCUMENTS

| | | | |
|---|---|---|---|
| 2002/0138154 A1* | 9/2002 | Li | A61L 31/12 424/428 |
| 2003/0199993 A1 | 10/2003 | Gellman et al. | |
| 2005/0209680 A1* | 9/2005 | Gale | A61L 31/148 623/1.15 |
| 2006/0229711 A1* | 10/2006 | Yan | A61F 2/82 623/1.38 |
| 2008/0097575 A1* | 4/2008 | Cottone | A61F 2/90 623/1.42 |
| 2009/0012596 A1* | 1/2009 | Kocur | A61F 2/856 623/1.35 |
| 2009/0012599 A1* | 1/2009 | Broome | A61F 2/856 623/1.35 |
| 2010/0016940 A1* | 1/2010 | Shokoohi | A61F 2/90 623/1.42 |
| 2012/0150275 A1 | 6/2012 | Shaw-Klein | |
| 2012/0209368 A1 | 8/2012 | Oepen et al. | |
| 2013/0158652 A1* | 6/2013 | Palasis | A61F 2/90 623/1.46 |

FOREIGN PATENT DOCUMENTS

| | | |
|---|---|---|
| WO | 2008137220 A1 | 11/2008 |
| WO | 2009009311 A2 | 1/2009 |
| WO | 2009009376 A2 | 1/2009 |
| WO | 2009155206 A2 | 12/2009 |

* cited by examiner

BIORESORBABLE STENT

CROSS-REFERENCE TO RELATED APPLICATIONS

German Patent Application 10 2013 004 625.4, filed Mar. 16, 2013, the complete disclosures of which are hereby incorporated herein by reference in their entirety for all purposes.

BACKGROUND OF THE INVENTION

Field of the Invention

The invention relates to a stent with a tubular framework structure having interconnected stent struts. The entire framework structure is made of a bioresorbable materials and is convertible from a compressed first geometric shape into a radially dilated, dimensionally stable tubular second geometric shape.

Description of the Prior Art

In vascular medicine, stents refer to medical implants for mechanical dilatation and support of hollow organs, in particular arterial blood vessels. For the purposes of the most gentle possible implantation, preferably by means of catheter support and minimally invasive surgical techniques, stents are typically made of a plastically deformable framework structure in tubular form, usually produced from metal or a metal alloy. The diameter of the tube is expandable from a small first diameter, at which it is possible to insert the stent without harming the patient and to position the stent inside the body, to a second larger tube diameter, at which the stent manifests its therapeutic effect for vascular support and radial vascular dilatation, in particular on stenosed sections of the vascular wall.

In addition to the desired therapeutic stent effect, adverse effects may also occur with the intracorporeal implantation of stents, which is usually permanent. These adverse effects originate from endogenous defensive reactions to the stent as a foreign body. Tissue irritation is unavoidable due to the force-activated mechanical contact between the radially dilated tubular framework structure of the stent and the vascular wall. Depending on the extent of this tissue irritation, it may cause inflammatory reactions, which can lead to the development of thromboses or restenoses. To counteract such medical complications, stents having biocompatible polymers or ceramics impregnated with medications, with coatings and/or with openings in the form of pores, are known, so that medications can be released into the vascular wall by diffusion. The publication WO 2012/057976 describes a stent having openings in the stent struts, comprising a polymer that contains a medication.

Due to the permanent implantation of stents, there is thus an increased risk of thrombi. To provide restriction of risk, it is at least recommended that concomitant antithrombotic medication be administered permanently.

Although the framework structure of a stent is permeable for solids and fluids due to its open-mesh framework structure, stents that are to be implanted in vascular regions, where there is a vascular branch covered by a portion of the open-mesh framework structure, nevertheless constitute significant obstacles to flow. To eliminate this problem, special stents have been developed for use in the main branches and side branches of human blood vessels. The publication US 2012/0209368 A1 describes a stent system and a method for implantation of same, in which the vascular side branch branching off from a main vascular branch is dilated by a separate stent to form a stent, which is situated along the main branch in the region of the outgoing side branch. However, the disadvantage of this special side branch stent system is that the large-volume implant leads to a substantial foreign body reaction and thus often results in relapse stenoses in the treated vascular region.

Alternative stent designs with large holes or recesses, so-called "open-cell designs" or "fenestrations," which are implemented in a stent described in the publication EP 2 497 444 A1, to create better access from a main vascular branch to corresponding side branches, have the disadvantage that vascular constrictions are constantly occurring due to tissue protrusions precisely at the locations where the stent body has a large hole or a fenestration.

The disadvantages associated with permanent stent implantation can be reduced with a new generic type of stent that has been known and in use for quite a while. These stents have stent struts made of bioresorbable, bioabsorbable or biocorrodible materials, which are capable of dissolving completely inside the body and therefore at least limit the period of time of physical stresses caused by the stent.

The publication WO 2009/155206 A2 discloses one such bioabsorbable stent made of a bioresorbable polyester, which is degraded successively in the body and/or dissolves completely over a period of time. A stent made of a magnesium alloy is described in the publication WO 2008/118607 A2. This stent also has properties of degradation by means of bioresorption or biocorrosion.

Use of dissolving bioresorbable stents leads first to an improvement in the biocompatibility problems that have occurred with the nondegradable stent materials known in the past as well as to a restriction in time on defensive physical reactions that cause the development of thromboses. Furthermore, it is no longer necessary to remove implanted stents by a surgical procedure, even if the procedure is only minimally invasive.

Nevertheless, the use of such stents is incapable of solving the problems associated with implantation inside a hollow organ in the region of at least one vascular branch, especially since a stent implanted in an arterial main vessel in the region of vascular branches or vascular outlets will also in this case displace the vascular outlets due to the stent struts and will thus have a permanent influence on the flow dynamics in this vascular region.

WO 2009/009376 A2 describes a stent having a bioresorbable membrane. The stent has a tubular framework structure comprised of a plurality of stent struts designed in the form of a meandering ring, connected to one another by connecting struts. The resulting framework structure of the stent encloses a surface region on the lateral surface that can be assigned to the stent, within which the framework structure deviates from the remaining framework structure of the stent. Thus, the stent struts situated inside the surface region are arranged and designed in such a way that they can be dilated to form a side stent structure oriented laterally to the stent and forming collars or also forming tubes. Nevertheless, the stent struts are surrounded by an additional bioresorbable membrane, both inside and outside the surface region, the stent ultimately implanted constitutes a permanent intracorporeal foreign body that causes irritation to the respective vascular area.

The publication WO 2009/009311 A2 describes a similar stent configuration, which has a tubular framework structure, which likewise, as in the present case, has a surface region bordered by a circumferential edge, within which a modified framework structure is provided to form a side stent structure that serves to support a vascular branch for the purpose of implantation in a vascular area having a vascular branch. Based on the finding that a stent structure designed for the purposes of implantation inside a vascular branching region experiences an increased mechanical stress to support the main vessel and the branching secondary stent to support the vascular branch, that is in the region of the circumferential edge mentioned above, the known stent configuration provides stent strut parts made of bioresorbable material in the region of the circumferential edge. Mechanical stress moments in the region of the transition between the main branch and the secondary branch of the stent configuration can be prevented by such stent strut components that dissolve automatically in the body. Likewise, the disadvantages associated with the stent sections located permanently in the respective vascular regions persist, as explained above.

The stents, which are disclosed in the publication DE 10 2010 027 124 A1, which are made of a biodegradable magnesium alloy, advantageously offer the possibility of being dissolved completely intracorporeally. Stents that dissolve completely intracorporeally have different dissolving properties because of their different absorption properties due to variations in the alloy composition (grain fineness) of the stent struts. The corrosion rate can thus be influenced in such a way that an implantation region dissolves more rapidly in the area of a bifurcation that is a vascular branch, than another implant region, so that the flow through the side vessel is ensured.

U.S. Pat. No. 8,109,991 B2 describes a stent that is not completely resorbable but instead has only bioresorbable connecting elements between individual annular stent elements. The connecting elements should dissolve to permit an improved adaptation of the stent to movements of the vessel and thus a reduction in complications.

US Published Patent Application Publication 2003/0 199 993 describes a bioresorbable implant that has different dissolving rates over time. The implant therefore has a layered structure comprised of different materials and particles may be introduced additionally into the individual layers. Different absorption rates can be adjusted locally in the implant due to local variations in the distribution of the particles.

US Patent Application Publication No. 2012/0150275 A1 discloses a bioresorbable stent that is created by printing an "ink-like" material on a carrier body. The special advantage of this method is that a seamless stent can be produced.

DE 10 2005 018 356 A1 relates to resorbable implants made of a resorbable base body and a biodegradable coating. The base body is a metal, a metal alloy, a metal salt, a polymer or mixtures of these compounds. However, the biodegradable coating preferably has biodegradable polymers and also contains at least one pharmacologically active substance.

DESCRIPTION OF THE INVENTION

The invention provides improvement of a stent for implantation in an intracorporeal vascular region having at least one vascular branch, such that it is ensured, first, that the at least one branching vascular channel is not covered by the implanted stent to thereby prevent a negative influence on the flow conditions, in particular in the region of the vascular branch and second, that the implanted stent causes little or no tissue irritation due to its foreign body properties, which reduces the risk of inflammation-induced thromboses altogether or at least the risk is reduced significantly on a long-term basis. The objective is to create the prerequisite that antithrombotic medication, which has so far been required for treatment of patients, is superfluous. Another aspect is to ensure prevention of stent fragments that have not dissolved completely in the process of decomposition of the stent from becoming detached from the remaining stent framework and entering the bloodstream as dangerous foreign bodies. Finally, it is possible to manufacture the stent as simply and thus inexpensively as possible.

The invention is based on a stent having a tubular framework structure having interconnected stent struts manufactured as a whole from a bioresorbable materials and which are convertible from a compressed first geometric shape to a radially dilated, dimensionally stable, tubular second geometric shape. With the framework structure made completely of bioresorbable material, this creates the prerequisite for prevention of irritation of the tissue regions in contact with the stent, which is associated with the implantation of a stent. This is the case in particular because the therapeutically effective lifetime of such a stent is limited. Through a suitable choice of materials to form the stent and/or providing a coating that delays bioresorption of the suitably selected stent material, the therapeutic lifetime of the stent can be defined almost precisely on the order of magnitude of years and/or months. The modification of such a stent made entirely of essentially known bioresorbable material(s) conditions the stent struts on a lateral surface that can be attributed to the tubular framework structure of the stent within at least a surface region that is cohesive in one piece, that is enclosed by an essentially closed circumferential edge, such that the stent struts are dissolved by bioresorption in a shorter period of time after implantation in a hollow organ in a patient than the stent struts outside of the at least one surface region. In this way, a lateral opening is formed within the tubular framework structure after the stent struts situated inside the surface region have completely dissolved. This opening is adapted in size and shape to the vascular branching within the hollow organ in which the stent has been implanted in a suitable way.

In the design and conditioning of the stent struts situated inside the circumferential edge, attention must be paid to the fact that no stent strut constituents that have not yet been completely bioresorbed become detached from the surrounding stent struts situated inside the surface region to thereby enter the bloodstream as foreign bodies from their complete dissolution by bioresorption. To rule out such separation phenomena, measures must be taken in accordance with the invention, so that stent struts within the surface region at the greatest distance from the circumferential edge are capable of dissolving within a shorter period of time than the stent struts that are close or directly adjacent to the circumferential edge.

According to the invention, the amount by weight of bioresorbable material per strut length of the stent struts decreases continuously or gradually within the surface region in increments which increase with the distance of the stent struts from the circumferential edge. Thus, for example, the stent struts situated centrally within the surface region have smaller stent diameters than the stent struts inside the surface region.

Alternatively, or in combination with the preceding measure, it is recommended that the different dissolving power of the stent struts within the surface region over time be accomplished by a suitable variation in the layer thickness of a bioresorbable material layer deposited on the stent struts the surface region. If, for example, the bioresorbable stent formed according to the invention is coated with a first material layer, which preferably has a uniform layer thickness on the coated regions of the framework structure and this coating is applied to the stent struts of the framework structure exclusive of the stent struts inside the surface region, then deposition of a second material layer on the stent struts inside the at least one surface region makes possible the different dissolving powers of the stent struts inside the surface region, as mentioned above, due to suitable variations in layer thickness. The layer thickness of the at least one second material layer is reduced continuously or gradually with an increase in the distance from the circumferential edge. This ensures that the stent struts inside the surface region will dissolve completely and the most rapidly by bioresorption are the farthest away from the circumferential edge enclosing the at least one surface region.

The stent of the invention is thus capable of, on the one hand, radially dilating the stenosed hollow organ after dissolving the respective stent struts that initially cover the vascular branch, and then, on the other hand, ensuring free lateral access to a secondary vessel branching off from the hollow organ.

Since the stent according to the invention differs only insignificantly or not at all from the known stents in the starting state, that is in the state prior to and during the process of implantation, so that the stent is handled in the same way using known minimally invasive surgical techniques. The process of radial dilatation by a balloon catheter, for example, after corresponding intracorporeal positioning of the stent does not differ from the dilatation of known stents. In intracorporeal positioning of the stent, the surgeon needs only to additionally account for the fact that the stent comes to be positioned axially and in its peripheral direction exactly opposite a lateral opening region of a vascular branch. The stent therefore has radiopaque markers that are attached suitably to the stent for marking the surface region, enabling the surgeon to position the stent accurately.

Since the complete framework structure of the stent dilating the hollow organ is manufactured of a bioresorbable material, the stent dissolves automatically and, along with it, the associated supporting function, so that the disadvantages associated with permanent retention of a stent inside a vessel are avoided. The maximum dwell time of the stent made of, bioabsorbable material can be defined through a suitable choice of material, shape and size for the design of the stent struts making up the framework structure.

To ensure that, after implantation, the stent struts situated inside the at least one surface region, as explained above, are subject to a more rapid dissolution by way of bioresorption than the remaining framework structure, the following measures are recommended as alternatives or to be used in combination:

A first possibility for rapid dissolution of the stent struts provided inside the surface region is to design the stent struts with a smaller amount of the weight of bioresorable material per predefined discrete strut length than the stent struts of the remaining framework structure directly or indirectly adjacent to the surface region outside the circumferential edge.

Since the bioresorption rate, that is the dissolving power over time, is predefined by the bioresorbable material itself, the implanted stent dissolves at a uniformly rapid rate over its entire spatial extent. Due to the smaller amount by weight per length of strut pertaining to the stent struts provided inside the surface region, these are capable of dissolving in a shorter amount of time than the stent struts in the remaining framework structure region within the area. One possible measure for reducing the amount by weight per length of strut pertaining to the stent struts provided inside the surface region, these are capable of dissolving in a shorter amount of time than the stent strut in the remaining framework structure region outside the area defined by the circumferential edge. One possible measure for reducing the amount by weight per strut length pertaining to the stent struts situated inside the surface region is to reduce the stent strut diameter in comparison with the stent struts situated outside of the surface region defined by the circumference. It is also sensible to design the stent struts to be hollow within the at least one surface region in comparison with a solid stent strut design in the remaining framework structure region of the stent outside the surface region. The latter measure makes it possible to design stent struts with a uniform stent strut diameter throughout the entire framework structure of the stent, so that a uniform structural stability can be implemented over the entire stent.

Another alternative measure for completely dissolving the stent struts situated inside the at least one surface region in a shorter period of time is to coat the framework structure having uniform bioresorbable material with an additional layer of material that delays the bioresorbability of the framework structure, except for the stent structures situated inside of the at least one surface region. Furthermore, the coating of the framework structure is not a complex and expensive measure in terms of the process technology, except for those stent struts situated outside the at least one predefined surface region with a material layer having a bioresorbability-reducing effect.

It is of course possible to combine the two measures described above, so that a stent having stent struts situated inside the at least one surface region that have a smaller amount by weight per length of strut in comparison with the remaining stent region is additionally coated with a material layer of a material having a bioresorbability-reducing effect so that the stent struts that are inside the at least one surface region are excluded from being coated with the material coating. A stent conditioned in this way has a longer lifetime in comparison with the stent struts that are situated inside the surface region and are therefore uncoated and are also designed to be thin, so that they are capable of dissolving completely after a suitably short implantation time and thus leading to a lateral opening inside the framework structure of the stent, which in this form ensures free and unhindered access to a vascular branch, while the vascular tissue directly surrounding the vascular branch remains inside the hollow organ, supported by the framework structure of the stent and/or dilated radially.

A third alternative for individual fabrication of the bioresorption behavior of the stent structures situated inside the at least one surface region in comparison with the stent struts of the remaining framework structure of the stent is to coat the stent struts, except for the stent struts situated inside the at least one predefined surface region, using at least one first bioresorbable material layer. The stent struts situated inside the at least one surface region is coated with at least one second bioresorbable material layer, which is completely bioresorbable in a shorter period of time than the first bioresorbable material layer.

The third alternative listed above can also be combined with the measure mentioned first, that is the stent struts situated inside the at least one surface region have a smaller amount by weight of bioresorbable material per strut length in comparison with the stent struts in the remaining stent region and which are also coated with the aforementioned material layer containing the at least one second bioresorbable material layer.

The at least one second bioresorbable material layer need not necessarily be a bioresorbable material that is different from the first bioresorbable material layer. Instead, it is possible to produce the first and second material layers from identical bioresorbable material, but in this case, the layer thickness of the bioresorbable material layer within the at least one surface region is to be selected to be smaller than the material layer of the first bioresorbable material layer in the remaining stent region. This ensures that the second material layer, which is designed to be thinner, will dissolve completely due to bioresorption after a suitable implantation time within a shorter period of time than the first bioresorbable material layer, which is designed to be thicker.

Implementations of the stent designed according to the invention are of course also possible, in which the at least one first layer of material and one second layer of material differ from one another in the type of material.

A preferred embodiment of the stent has a tubular framework structure, which has a uniform framework structure. That is the stent struts have a uniform mesh pattern or arrangement pattern and enclose open framework structure meshes having a geometric repeating period and these meshes preferably have a uniform mesh size. For economic reasons as well as for reasons of access to known and proven manufacturing techniques, all stent struts forming the framework structure are produced from a uniform bioabsorbable material and can be joined together in one piece, depending on the type of fabrication, or joined and/or woven together in the form of a braid to form a braided framework structure.

The size and shape of the tubular stents are to be selected in accordance with the size and shape of the hollow organ to be treated. This is also true in particular for the number of surface regions to be provided along the lateral surface of the tubular stent as well as their size and shape, which are to be selected accordingly based on the different vascular branches leading away from the hollow organ at the side. Thus, depending on the size and shape of the vascular branch, the circumferential edge enclosing the at least one surface region may be circular, elliptical or oval or may have an n-angular shape, where n is a natural number 23. The circumferential edge may be embodied as a virtual bordering line that is a line that is not physically viewable. This is the case when the framework structure has a homogeneously permeable mesh structure with the stent struts being designed in one piece and being continuous in the transition to the at least one surface region. Likewise, the surface region may be surrounded by a circumferential edge in the form of a closed stent structure, which, however, is designed in such a way that it permits radial dilatation of the stent.

It is of course also possible to combine the preceding measures with respect to the deposition of the material layer(s) with the various embodiments of amount by weight per strut length of the stent struts.

BRIEF DESCRIPTION OF THE DRAWINGS

The invention will be described below as an example without restriction of the invention on the basis of exemplary embodiments with reference to the drawings, in which.

DETAILED DESCRIPTION OF THE INVENTION

Figure 1A:
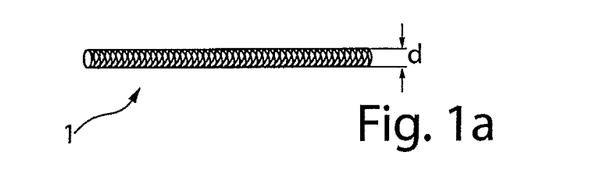
FIGS. 1a, b and c show schematic diagrams of a stent designed according to the invention.
Figure 1B:
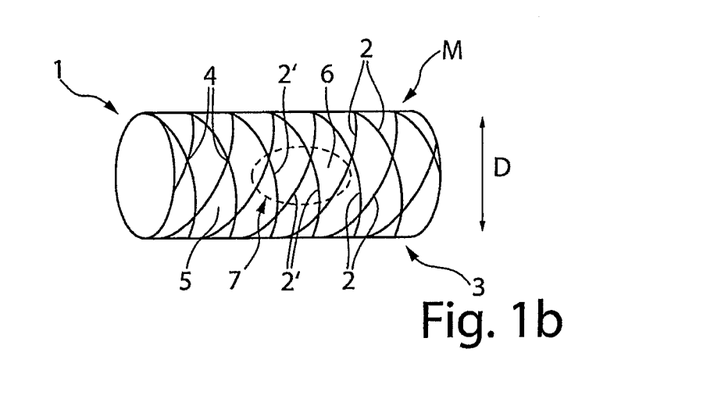

FIG. 1a shows a highly schematic diagram of a tubular stent 1, having a stent diameter d which has not been dilated radially. FIG. 1b shows the same stent in a radially dilated form with a stent diameter D>d. The stent 1 has a framework structure 3 made of stent struts 2 (see FIG. 1b), which, as a whole, consists of a bioresorbable material. The individual stent struts 2 making up the framework structure 3 are loosely or tightly connected to one another at connection points 4 and each encloses framework meshes 5 designed to be open. The individual stent struts 2 forming the framework structure 3 preferably are a bioresorbable metal or a bioresorbable metal alloy. The metal is one of the metals listed below, or the metal alloy contains at least one metal chosen from the following metals: magnesium, zinc, zirconium, carbon, iron, sodium, calcium, manganese, molybdenum or selenium. It is also possible to fabricate the stent struts 2 from a bioresorbable polymer of the family of poly-(L-lactides), poly-lactide-co-glycolides or poly-glycolactides, polycarbonates, polychitosans or phospholipids. Through the choice of material as well as the material thickness of the individual fabricated stent struts, the dissolution properties can be determined in advance by way of bioresorption of the stent after implantation inside the body. It is thus possible in particular to define and stipulate the therapeutic duration of effect of the implanted stent in advance, that is to stipulate in advance the number of years and/or months, after which the stent 1 will lose its therapeutic effect of dilating the hollow organ after implantation and then dissolve completely ultimately by way of bioresorption.

In contrast with known stents, which dissolve completely by way of bioresorption, the stent designed according to the invention has a surface region 6 which is situated on the lateral surface M of the geometric shape of the stent 1, which is designed in the form of a tube or a hollow cylinder. The surface region is surrounded by a virtual or real circumferential edge 7 and separates the surface regions 6 from the stent struts of the remaining framework structure of the stent 1. In the case of the exemplary embodiment illustrated in FIGS. 1a and b, the circumferential edge 7 is designed to be oval. FIG. 1b shows the stent 1 in a radially dilated state, which is assumed by the stent 1 after the process of implantation and radial dilatation. The stent struts 2' situated inside the surface region 6 differ from the stent struts 2 situated outside of the surface regions 6 in that they are capable of dissolving in a shorter period of time after intracorporeal implantation than the stent struts 2 outside of the surface region 6 defined by the circumferential edge 7. That is the stent struts 2' are capable of dissolving in a chronological order, from the center out to the circumferential edge 7, within of the surface region 6.

Figure 1C:
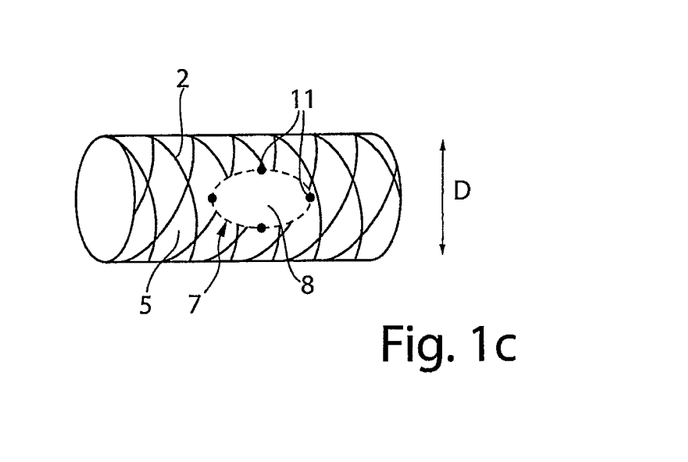

FIG. 1c shows the situation after complete dissolution of the stent struts 2', which are situated inside the surface region 6. The opening 8, which is inscribed by the circumferential edge 7, serves to provide free access to a vascular branch from a hollow organ within which the stent 1 is positioned for dilatation of the hollow organ radially. The shape and size of the opening 8 are adapted to the shape and width of the opening of the vascular branch, so that the flow conditions, which prevail in the region of the vascular branch, are not impaired.

Radiopaque markers 11 are provided along the circumferential edge 7, enabling the surgeon to position the stent 1 accurately in relation to a vascular branch.

Depending on the anatomy of the hollow organs to be treated, in deviation from the exemplary embodiment illustrated in FIG. 1, a plurality of surface regions 6 and/or the resulting free openings 8 may be provided within a stent 1.

Figure 2A:
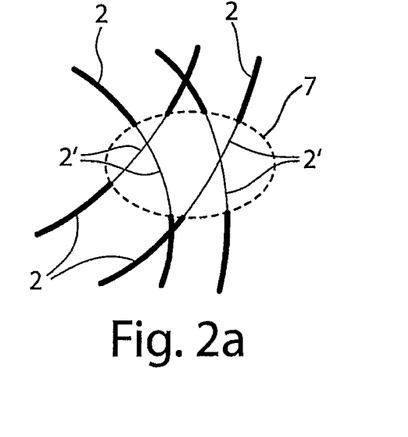
FIGS. 2a, b, c, d and e show schematic diagrams of possible embodiments to form stent struts inside the at least one surface region.

The schematic detailed diagrams of the surface region 6 surrounded by the circumferential edge 7 shown in FIGS. 2*a* though 2*e* are explained on the basis of the alternative measures, by which dissolution of the stent struts 2' within the surface region 6 is achieved within a shorter period of time in comparison with the amount of time required to completely dissolve the framework structure 3 of the stent 1 by bioresorption.

A first embodiment illustrated in FIG. 2*a* shows the design of stent struts 2' situated inside the surface region 6 and having a smaller stent strut diameter in comparison with the stent strut diameter of the stent struts 2 adjacent to the circumferential edge 7 of the surface region 6 and outside. Because of the smaller amount 6 by weight on the outside per stent strut length of the stent struts 2', which are manufactured of otherwise the same bioresorbable material as the stent struts 2 adjacent to the surface area, it is ensured that the stent struts 2' will be completely dissolved after an extremely short period of time, that is within a few weeks or months and will thus result in a free opening 8. The difference due to the difference in the stent strut diameters with respect to the amount by weight of bioresorbable material per strut length can amount to at least 1% up to max. 60% between the stent struts 2' situated inside of the surface region and the stent struts 2 adjacent to and outside the circumferential edge 7 of the surface region 6.

Figure 2B:
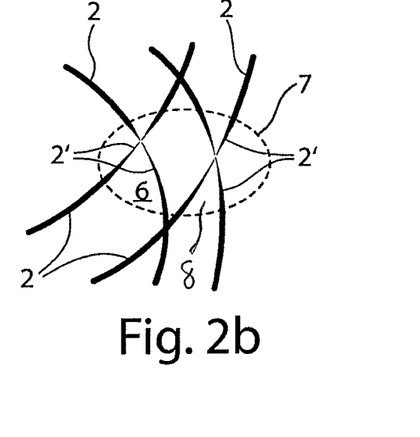

An improved embodiment according to the invention, in comparison with the example illustrated in FIG. 2*a*, is shown in FIG. 2*b*. Again in this case, the stent strut diameters of the stent struts 2' are designed to be smaller in comparison with the stent struts 2 outside of the surface region 6 defined by the circumferential edge 7. The stent strut diameter additionally is varied continuously, so that the stent strut diameter of the stent struts 2' decreases with an increase inwardly from the circumferential edge 7 in distance. The difference in the stent strut diameters with respect to the amount by weight of bioresorbable material per strut length may amount to at least 1% up to max. 60% between the stent struts 2' situated radially at a distance inwardly from the circumferential edge 7 and the stent struts 2' close to the circumferential edge. This measure ensures that the stent struts 2' situated inside the surface region 6 are capable of completely dissolving, beginning at their greatest inward distance from the circumferential edge 7, until finally the stent struts 2' have reached the circumferential edge 7 by dissolving spontaneously by way of bioresorption and thus forming the free opening. It is possible in this way to rule out partial separation of stent strut portions within the surface region 6.

Figure 2C:
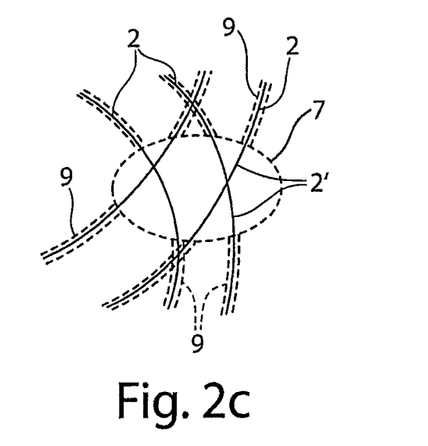

Another possibility for time-controlled bioresorption of the stent 1 designed according to the invention is illustrated in FIG. 2*c*, where the stent struts 2 situated outside of the surface region 6 defined by the circumferential edge 7 are coated with a first material layer 9, while the stent struts 2' situated inside the surface region 6 defined by the circumferential edge are not coated and are designed in the same way as those in FIG. 2*b*. It is obvious that the additional material layer 9 results in prolonging bioresorption, so that the uncoated stent strut portions 2' are completely absorbed within the surface region 6 in a shorter period of time.

Figure 2D:
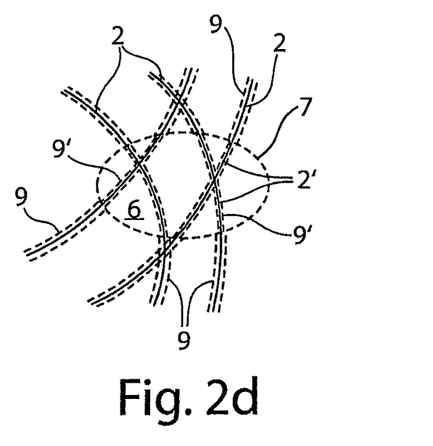
Figure 2E:
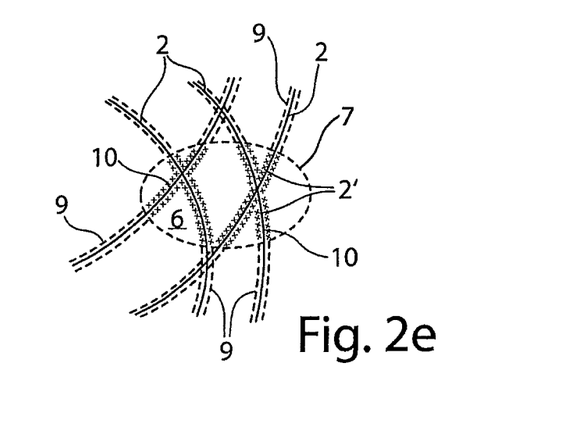

Another embodiment shown in FIG. 2*d* provides for both the stent struts 2 and the stent struts 2' situated inside the surface region 6 to be coated with a material layer of a uniform material, while the stent struts 2' situated inside the surface region 6 are coated with a thinner layer of material than the stent struts 2 outside of the surface region 6. The thinner layer of material 9' also has a continuously decreasing material layer thickness the greater the distance along the stint struts 2' situated inside the surface region 6 from the circumferential edge 7. Due to the thinner layer thickness formation of the material layer 9' on the stent struts 2' inside the surface region 6, which should amount to 1% to max. 60% of the material layer thickness of the material layer 9 outside of the surface region 6, precisely the layer of material 9' is dissolved in a shorter period of time than the material layer 9 on the stent struts 2 outside of the surface region 6. It is again ensured that the stent struts 2' inside the circumferential edge are resorbed in a shorter period of time than the adjacent stent struts 2 outside the circumferential edge. The decreasing thickness of the material layer 9' inwardly toward the center of the surface region 6 from the circumferential edge also ensures that the stent struts 2' near the center inside the surface region 6 are the first to begin dissolving so that the resulting opening within the stent struts 2' dilates radially outward toward the circumferential edge 7 causing the continuous resorption of material. The stent struts 2' situated inside the surface region 6 taper in an advantageous, although not essential, manner with an increase in the distance inward from the circumferential edge 7, as illustrated in the exemplary embodiment according to FIG. 2*b*. In this case, however, it is also possible that the effect described here of the dilatation opening from the inside radially to the outside is also established due to the presence of the second material layer 9' if the stent struts 2' have a uniform, thin stent strut diameter.

Due to the preferably uniform radial dilatation of the stent strut opening, it is impossible for individual parts to be detached from the stent strut structure network and to enter the bloodstream as foreign bodies and be able to travel around there in an uncontrolled manner. It is also impossible to additionally apply different layered materials to the stent struts 2 and 2' in addition to the choice of thickness of the material layers to be applied to the stent struts 2 and 2', respectively. Care should be taken to ensure that the layer material 10 applied to the stent struts 2' inside of the surface region 6 is resorbable more rapidly than the layer material 9 on the stent struts 2 (see FIG. 2*e*). Furthermore, it is also advantageous to design the at least one second bioresorbable material layer 10 as a bioresorbable polymer layer which holds and releases at least one medication. The at least one medication may preferably be selected from the class of antiproliferative substances, the limus group, such as sirolimus, everolimus, zotarolimus, the substance class of statins, P2Y12 antagonists or thrombin antagonists.

The alternative design options described above for the purpose of a time-staggered dissolution of the stent struts 2 and 2' can be combined in any suitable manner.

LIST OF REFERENCE NUMERALS

1 stent
2 stent struts
2' stent struts inside the surface region
3 framework structure
4 connecting spot
5 mesh opening
6 surface region 7 circumferential edge
8 opening
9 first material layer
9' first material layer with a small material layer thickness
10 second material layer
11 radiopaque marker

The invention claimed is:

1. A tubular framework configured to radially dilate a hollow organ and provide lateral access to a vessel branching laterally from the hollow organ comprising:
   stent struts which are interconnected and fabricated from at least one bioresorbable material with the framework being convertible from a first compressed geometric shape into a radially dilated dimensionally stable tubular shape;
   all stent struts of the tubular framework structure being made from a uniform bioresorbable material;
   at least one surface region which is a single piece surrounded by a circumference and is located on a cylindrical surface of the tubular framework, the at least one surface region including stent struts which are interconnected with stent struts which are located adjacent to the at least one surface region;
   the stent struts in the at least one surface region having a weight of the bioresorbable material per unit length of strut which is less than a weight of the bioresorbable material per unit of length of stent struts adjacent to the at least one surface region;
   an amount by weight of bioresorbable material per strut length of the stent struts within the at least one surface region decreasing with an increase in distance of the stent struts from the circumference or stent struts adjacent to the at least one surface region are coated with at least one first bioresorbable material layer, stent struts inside the at least one surface region are coated with at least one second bioresorbable material layer and will be bioresorbed in a shorter period of time than the first bioresorbable material layer, and a thickness of a layer of the at least one second material layer decreases continuously with an increase in distance of the stent struts coated with the second material layer from the circumference; and
   the stent struts inside the at least one surface area are bioabsorbable and configured to form an opening covering the at least one surface region to the another vessel branching laterally from the hollow organ beginning within the at least one surface region at a greatest distance from the circumference and extending towards the circumference before completion of bioabsorption of the stent struts adjacent to the at least one surface area without introduction occurring of parts of the stent struts within the at least one surface area into the hollow organ or the vessel during the bioabsorption of the stent struts and wherein
   at least one of at least two stent struts inside the at least one surface region have an amount of bioabsorbable material per strut length differing from another stent strut inside the at least one surface region by at least 1% to a maximum of 60%; and
   at least two stent struts inside the at least one surface region are coated with the second material layer, with thicknesses of the material layers differing from one another by at least 1% to a maximum of 60%.

2. The tubular framework according to claim 1, wherein the tubular framework structure has a uniform framework structure.

3. The tubular framework according to claim 2, wherein the stent struts are connected and enclose an open framework structure mesh, and all of the framework structure meshes have an uniform shape.

4. A tubular framework according to claim 3, wherein:
   the circumference is circular, elliptical, oval or has n angles on a periphery with n being >3.

5. The tubular framework according to claim 3, wherein:
   the stent struts in the at least one surface region are uncoated.

6. A tubular framework according to claim 5, wherein:
   the bioresorbable material is one of a metal and a metal alloy wherein the metal or metal alloy contains at least one element of magnesium, zinc, zirconium, carbon, iron, sodium, calcium, manganese, molybdenum or selenium.

7. A tubular framework according to claim 2, wherein:
   the circumference is circular, elliptical, oval or has n angles on a periphery with n being >3.

8. The tubular framework according to claim 2, wherein:
   the stent struts in the at least one surface region are uncoated.

9. A tubular framework according to claim 8, comprising:
   at least one radiopaque marker disposed along the circumference.

10. A tubular framework according to claim 2, wherein:
   the stent struts have a smaller diameter in the at least one surface region than a diameter of the stent struts adjacent to the at least one surface region.

11. A tubular framework according to claim 2, comprising:
   at least one radiopaque marker disposed along the circumference.

12. A tubular framework according to claim 2, wherein:
   the bioresorbable material is one of a metal and a metal alloy wherein the metal or metal alloy comprises at least one element of magnesium, zinc, zirconium, carbon, iron, sodium, calcium, manganese, molybdenum or selenium.

13. The tubular framework according to claim 1, wherein the stent struts are connected and enclose an open framework structure mesh, and all of the framework structure meshes have a uniform shape.

14. A tubular framework according to claim 13, wherein:
   the circumference is circular, elliptical, oval or has n angles on a periphery with n being >3.

15. A tubular framework according to claim 14, comprising:
   at least one radiopaque marker disposed along the circumference.

16. The tubular framework according to claim 13, wherein:
   the stent struts in the at least one surface region are uncoated.

17. A tubular framework according to claim 16, comprising:
   at least one radiopaque marker disposed along the circumference.

18. A tubular framework according to claim 13, wherein:
   the stent struts have a smaller diameter in the at least one surface region than a diameter of the stent struts adjacent to the at least one surface region.

19. A tubular framework according to claim 13, comprising:
   at least one radiopaque marker disposed along the circumference.

20. A tubular framework according to claim 13, wherein:
the bioresorbable material is one of a metal and a metal alloy wherein the metal or metal alloy contains at least one element of magnesium, zinc, zirconium, carbon, iron, sodium, calcium, manganese, molybdenum or selenium.

21. A tubular framework according to claim 1, wherein:
the circumference is circular, elliptical, oval or has n angles on a periphery with n being >3.

22. A tubular framework according to claim 21, comprising:
at least one radiopaque marker disposed along the circumference.

23. A tubular framework according to claim 21, wherein:
the bioresorbable material is one of a metal and a metal alloy wherein the metal or metal alloy contains at least one element of magnesium, zinc, zirconium, carbon, iron, sodium, calcium, manganese, molybdenum or selenium.

24. The tubular framework according to claim 1, wherein:
the stent struts in the at least one surface region are uncoated.

25. A tubular framework according to claim 24, wherein:
the stent struts have a smaller diameter in the at least one surface region than a diameter of the stent struts adjacent to the at least one surface region.

26. A tubular framework according to claim 25, wherein:
the bioresorbable material is one of a metal and a metal alloy wherein the metal or metal alloy contains at least one element of magnesium, zinc, zirconium, carbon, iron, sodium, calcium, manganese, molybdenum or selenium.

27. A tubular framework according to claim 24, wherein:
the bioresorbable material is one of a metal and a metal alloy wherein the metal or metal alloy contains at least one element of magnesium, zinc, zirconium, carbon, iron, sodium, calcium, manganese, molybdenum or selenium.

28. A tubular framework according to claim 1, wherein:
the stent struts have a smaller diameter in the at least one surface region than a diameter of the stent struts adjacent to the at least one surface region.

29. A tubular framework according to claim 1, comprising:
at least one radiopaque marker disposed along the circumference.

30. A tubular framework according to claim 1, wherein:
the bioresorbable material is one of a metal and a metal alloy wherein the metal contains at least one element of magnesium, zinc, zirconium, carbon, iron, sodium, calcium, manganese, molybdenum or selenium.

31. A tubular framework according to claim 1, wherein:
the bioresorbable material comprises one of bioresorbable polymers of a family of poly (L-lactides), polylactide-co-glycolides, poly-glyco-lactides, polycarbonates, poly-chitosans or phospho-lipids.

32. A tubular framework according to claim 1, wherein:
the second bioresorbable material layer is a bioresorbable polymer layer which holds and releases at least one medication.

33. A tubular framework according to claim 1, wherein:
the at least one medication is selected from a group of a antiproliferative substance class of a limus group comprising at least one of sirolimus, everolimus, zotarolimus, a substance class of statins, and P2Y12 antagonists or thrombin antagonists.

34. A tubular framework configured to radially dilate a hollow organ and provide lateral access to a vessel branching laterally from the hollow organ comprising:
stent struts which are interconnected and fabricated from at least one bioresorbable material with the framework being convertible from a first compressed geometric shape into a radially dilated dimensionally stable tubular shape;
all stent struts of the tubular framework structure being made from a uniform bioresorbable material;
at least one surface region which is a single piece surrounded by a circumference and is located on a cylindrical surface of the tubular framework, the at least one surface region including stent struts which are interconnected with stent struts which are located adjacent to the at least one surface region;
stent struts in the at least one surface region having a weight of the bioresorbable material per unit length of strut which is less than a weight of the bioresorbable material per unit of length of stent struts adjacent to the at least one surface region; and wherein
the stent struts inside the at least one surface area are bioabsorbable and configured to form an opening covering the at least one surface region to the another vessel branching laterally from the hollow organ beginning within the at least one surface region at a greatest distance from the circumference and extending towards the circumference before completion of bioabsorption of the stent struts adjacent to the at least one surface area without introduction occurring of parts of the stent struts within the at least one surface area into the hollow organ or the vessel during the bioabsorption of the stent struts, and wherein
at least one of at least two stent struts inside the at least one surface region have an amount of bioabsorbable material per strut length differing from another stent strut inside the at least one surface region by at least 1% to a maximum of 60%; and at least two stent struts inside the at least one surface region are coated with the second material layer, with thicknesses of the material layers differing from one another by at least 1% to a maximum of 60%.

* * * * *